US010056079B2

(12) United States Patent
Matsumoto et al.

(10) Patent No.: US 10,056,079 B2
(45) Date of Patent: Aug. 21, 2018

(54) IN-VEHICLE DEVICE, SERVER DEVICE, INFORMATION SYSTEM, AND CONTENT START METHOD

(71) Applicant: Clarion Co., Ltd., Saitama-shi, Saitama (JP)

(72) Inventors: Yusuke Matsumoto, Saitama (JP); Takuya Fujieda, Tokyo (JP); Noriyuki Abe, Yokohama (JP); Makoto Orino, Saitama (JP); Kimio Okamoto, Yokohama (JP)

(73) Assignee: Clarion Co., Ltd., Saitama-shi (JP)

( * ) Notice: Subject to any disclaimer, the term of this patent is extended or adjusted under 35 U.S.C. 154(b) by 0 days.

(21) Appl. No.: 15/203,052

(22) Filed: Jul. 6, 2016

(65) Prior Publication Data
US 2017/0011743 A1    Jan. 12, 2017

(30) Foreign Application Priority Data

Jul. 7, 2015    (JP) ................................ 2015-135925

(51) Int. Cl.
| G10L 15/065 | (2013.01) |
| G10L 15/20 | (2006.01) |
| G06F 3/048 | (2013.01) |
| G10L 21/00 | (2013.01) |
| G10L 15/22 | (2006.01) |

(Continued)

(52) U.S. Cl.
CPC .............. *G10L 15/22* (2013.01); *G10L 15/08* (2013.01); *G10L 15/24* (2013.01); *G10L 15/30* (2013.01); *G01C 21/3629* (2013.01); *G01C 21/3697* (2013.01); *G10L 2015/088* (2013.01); *G10L 2015/223* (2013.01)

(58) Field of Classification Search
CPC ....... G10L 15/065; G10L 15/20; G10L 21/00; G06F 3/048
USPC .................. 704/225, 233, 235, 275; 715/834
See application file for complete search history.

(56) References Cited

U.S. PATENT DOCUMENTS

| 6,330,499 B1 * | 12/2001 | Chou ..................... G07C 5/008 |
| | | 701/31.4 |
| 2002/0103582 A1 * | 8/2002 | Ohmura ................. G07C 5/008 |
| | | 701/31.4 |

(Continued)

FOREIGN PATENT DOCUMENTS

| JP | 2002-366166 A | 12/2002 |
| JP | 2006-146630 A | 6/2006 |

(Continued)

OTHER PUBLICATIONS

European Search Report issued in counterpart European Application No. 16001516.0 dated Dec. 13, 2016 (11 pages).

(Continued)

*Primary Examiner* — Seong Ah A Shin
(74) *Attorney, Agent, or Firm* — Crowell & Moring LLP

(57) ABSTRACT

An in-vehicle device according to the present invention includes a voice input receiving unit that receives input information with a voice, an output control unit that transmits the input information to a predetermined external device, and then outputs a plurality of received content candidates according to order of a priority degree of the content candidates, and a content execution unit that executes the content candidate upon receipt of specification of any of the output content candidates.

12 Claims, 16 Drawing Sheets

(51) Int. Cl.
*G10L 15/08* (2006.01)
*G10L 15/24* (2013.01)
*G10L 15/30* (2013.01)
*G01C 21/36* (2006.01)

(56) References Cited

U.S. PATENT DOCUMENTS

| | | | |
|---|---|---|---|
| 2002/0188455 A1 | 12/2002 | Shioda et al. | |
| 2005/0202845 A1* | 9/2005 | Sasaki | G08G 1/096716 455/556.2 |
| 2006/0248075 A1 | 11/2006 | Shimomori et al. | |
| 2007/0005368 A1* | 1/2007 | Chutorash | B60R 16/0373 704/275 |
| 2008/0280655 A1* | 11/2008 | Ozaki | G01C 21/26 455/569.2 |
| 2009/0083029 A1 | 3/2009 | Doi et al. | |
| 2009/0234648 A1* | 9/2009 | Nagatomo | G10L 15/22 704/235 |
| 2010/0218141 A1* | 8/2010 | Xu | G06F 3/04817 715/834 |
| 2012/0016678 A1* | 1/2012 | Gruber | G06F 17/3087 704/275 |
| 2012/0089942 A1* | 4/2012 | Gammon | G06F 3/048 715/784 |
| 2012/0245934 A1* | 9/2012 | Talwar | G10L 15/22 704/235 |
| 2012/0245945 A1* | 9/2012 | Miyauchi | G10L 15/06 704/275 |
| 2012/0259951 A1 | 10/2012 | Schalk et al. | |
| 2012/0330651 A1* | 12/2012 | Obuchi | G10L 15/01 704/225 |
| 2014/0024334 A1* | 1/2014 | Berry | G08G 1/205 455/404.2 |
| 2014/0258302 A1 | 9/2014 | Iizuka | |
| 2014/0278395 A1* | 9/2014 | Zurek | G10L 15/065 704/233 |
| 2014/0306838 A1* | 10/2014 | Beumler | B60N 2/28 340/988 |
| 2015/0153570 A1* | 6/2015 | Yamamoto | H04M 1/72563 345/184 |
| 2015/0269939 A1* | 9/2015 | Gruchalski | B60R 16/0373 704/251 |
| 2015/0331664 A1* | 11/2015 | Osawa | G01C 21/3608 704/275 |

FOREIGN PATENT DOCUMENTS

| | | |
|---|---|---|
| JP | 2006-311462 A | 11/2006 |
| JP | 2008-241943 A | 10/2008 |
| JP | 2009-80579 A | 4/2009 |
| WO | WO 2013/118592 A1 | 8/2013 |

OTHER PUBLICATIONS

Bradesko et al., "The Architecture of Future Automotive Applications based on Web Technologies", Oct. 29, 2012, pp. 1-5, XP055203658, http://www.w3.org/2012/11/web-and-automotive/submissions/webautomotive1_submission_24.pdf.

* cited by examiner

FIG.4

KEYWORD STORAGE UNIT 221

| WORD NUMBER (221A) | WORD (221B) | RELATED CONTENT NAME (221C) | RELATED WORD NUMBER (221D) |
|---|---|---|---|
| 1 | EXPRESSWAY | ROUTE SEARCH | 2,3,4 |
| 2 | ROAD | ROUTE SEARCH | 1,5 |
| 3 | SERVICE AREA | SA/PA SEARCH | 1,6,7,8 |
| 4 | FAST | — | 1,9 |
| 5 | GENERAL ROAD | SIDE ROAD SEARCH | 2 |
| 6 | REST | REST SPOT SEARCH | 3,8 |
| 7 | SOUVENIR | LOCAL GOURMET SEARCH | 3 |
| 8 | BATHROOM | BATHROOM SEARCH | 3,6 |
| 9 | SPEED | — | 4 |
| ... | ... | ... | ... |

CONTENT CATEGORY STORAGE UNIT 222

| NUMBER | CONTENT | CATEGORY |
|---|---|---|
| 1 | ROUTE SEARCH | NAVIGATION |
| 2 | SA/PA SEARCH | REST |
| 3 | SIDE ROAD SEARCH | NAVIGATION |
| 4 | REST SPOT SEARCH | REST |
| 5 | LOCAL GOURMET SEARCH | GOURMET |
| 6 | BATHROOM SEARCH | URGENCY |
| ... | ... | ... |

FIG.6

PRIORITY CATEGORY STORAGE UNIT 223

| NUMBER (223A) | BIOLOGICAL STATE INFORMATION (223B) | CATEGORY TO BE PRIORITIZED (223C) | PRIORITY DEGREE INCREASE AMOUNT (223D) |
|---|---|---|---|
| 1 | AROUSAL LEVEL DECREASE A | REST | 3 |
| 2 | BAD HEALTH A | HEALTH | 3 |
| 3 | AROUSAL LEVEL DECREASE B | REST | 2 |
| 4 | BAD HEALTH B | HEALTH | 2 |
| 5 | ATTENTION DISTRACTION A | URGENCY | 2 |
| 6 | AROUSAL LEVEL DECREASE C | REST | 1 |
| ... | ... | ... | ... |

FIG.8

RELATED WORD TEMPORARY STORAGE UNIT 225

| INPUT WORD | FIRST RELATED WORD | SECOND RELATED WORD | RELATED CONTENT NAME | CATEGORY |
|---|---|---|---|---|
| EXPRESSWAY | — | — | ROUTE SEARCH | NAVIGATION |
| | ROAD | — | ROUTE SEARCH | NAVIGATION |
| | SERVICE AREA | — | SA/PA SEARCH | REST |
| | FAST | — | — | — |
| | | GENERAL ROAD | SIDE ROAD SEARCH | NAVIGATION |
| | | REST | REST SPOT SEARCH | REST |
| | | SOUVENIR | LOCAL GOURMET SEARCH | GOURMET |
| | | BATHROOM | BATHROOM SEARCH | URGENCY |
| | | SPEED | — | — |
| ... | ... | ... | ... | ... |

CONTENT PRIORITY DEGREE TEMPORARY STORAGE UNIT 226

226A     226B     226C

| CONTENT | CATEGORY | PRIORITY DEGREE |
|---|---|---|
| ROUTE SEARCH | NAVIGATION | 1 |
| ROUTE SEARCH | NAVIGATION | 1 |
| SA/PA SEARCH | REST | 1 |
| SIDE ROAD SEARCH | NAVIGATION | 1 |
| REST SPOT SEARCH | REST | 1 |
| LOCAL GOURMET SEARCH | GOURMET | 1 |
| BATHROOM SEARCH | URGENCY | 1 |
| ... | ... | ... |

⇩ EXCLUDE OVERLAPPING CONTENT AND INCREASE PRIORITY DEGREE

| CONTENT | CATEGORY | PRIORITY DEGREE | |
|---|---|---|---|
| ROUTE SEARCH | NAVIGATION | 1+1 | 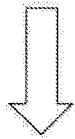 226D |
| SA/PA SEARCH | REST | 1 | |
| SIDE ROAD SEARCH | NAVIGATION | 1 | |
| REST SPOT SEARCH | REST | 1 | |
| LOCAL GOURMET SEARCH | GOURMET | 1 | |
| BATHROOM SEARCH | URGENCY | 1 | |

FIG.10

CONTENT PRIORITY DEGREE TEMPORARY STORAGE UNIT 226

| 226A<br>CONTENT | 226B<br>CATEGORY | 226C<br>RIORITY DEGREE |
|---|---|---|
| ROUTE SEARCH | NAVIGATION | 1+1 |
| SA/PA SEARCH | REST | 1 |
| SIDE ROAD SEARCH | NAVIGATION | 1 |
| REST SPOT SEARCH | REST | 1 |
| LOCAL GOURMET SEARCH | GOURMET | 1 |
| BATHROOM SEARCH | URGENCY | 1 |

⇩ INCREASE PRIORITY DEGREE OF CATEGORY ACCORDING TO BIOLOGICAL STATE

| CONTENT | CATEGORY | RIORITY DEGREE |
|---|---|---|
| ROUTE SEARCH | NAVIGATION | 2 |
| SA/PA SEARCH | REST | 1+3 |
| SIDE ROAD SEARCH | NAVIGATION | 1 |
| REST SPOT SEARCH | REST | 1+3 |
| LOCAL GOURMET SEARCH | GOURMET | 1 |
| BATHROOM SEARCH | URGENCY | 1 |

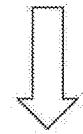
226E
226F

TWO-STAGE SEARCH EXAMPLE

FIG.15

WORD CONVERSION TABLE STORAGE UNIT 224

| NUMBER | ENVIRONMENT INFORMATION | THRESHOLD | WORD |
|---|---|---|---|
| 1 | VEHICLE SPEED | AVERAGE VALUE IS CHANGED FROM LESS THAN 70 TO 70 OR MORE | EXPRESSWAY |
| 2 | VEHICLE SPEED | AVERAGE VALUE IS CHANGED FROM 70 OR MORE TO LESS THAN 70 | GENERAL ROAD |
| 3 | WINDSHIELD WIPER | ON-TIME IS 5 SECONDS OR MORE | RAIN |
| 4 | HEADLIGHTS | ON-TIME IS 5 SECONDS OR MORE | AFTERNOON |
| 5 | DRIVING TIME | 1 HOUR OR MORE | LONG-TIME DRIVING |
| 6 | TIME TO DESTINATION | 1 HOUR OR MORE | FAR |
| 7 | TIME TO DESTINATION | WITHIN 10 MINUTES | ARRIVAL |
| 8 | TRAFFIC JAM INFORMATION | CHANGE FROM NON-TRAFFIC JAM STATE TO TRAFFIC JAM STATE | TRAFFIC JAM |
| 9 | GAS REMAINING AMOUNT | CHANGE FROM 20% OR MORE TO LESS THAN 20% | GAS SHORTAGE |
| 10 | HUNGRY | YES | HUNGRY |
| 11 | BAD HEALTH | YES | POOR |
| 12 | AROUSAL LEVEL DECREASE | YES | SLEEPY |
| 13 | TEMPERATURE | CHANGE FROM LESS THAN 30 DEGREES C TO 30 DEGREES C OR MORE | HOT |
| 14 | CAMERA RECOGNITION INFORMATION | THERE IS OBJECT IN FRONT | DANGER |
| 15 | DISASTER WARNINGS | YES | DISASTER |
| 16 | GESTURE | ROTATION AROUND Y AXIS BY 60 DEGREES | LATEST INFORMATION |
| ... | ... | ... | ... |

IN-VEHICLE DEVICE, SERVER DEVICE, INFORMATION SYSTEM, AND CONTENT START METHOD

BACKGROUND

Technical Field

The present invention relates to a technology of an in-vehicle device, a server device, an information system, and a content start method.

Related Art

Conventionally, a technology about a content providing system including analysis means that collects and analyzes conversation of a user and outputs an analysis result, content acquisition means that acquires content from a content database based on the analysis result, and content providing means that provides the acquired content to the user is described in JP 2002-366166 A.

SUMMARY OF THE INVENTION

The above-described technology changes content to be provided, by grasping an environment where the user has a conversation according to a sound volume and a frequency. However, the technology does not enhance accuracy to identify content actually desired by the user, and does not necessarily contribute to convenience of the user.

An objective of the present invention is to provide a technology for starting appropriate content according to details input with a voice.

The present invention includes a plurality of means for solving at least a part of the problem. However, an example is as follows. To solve the above-problem, an in-vehicle device according to the present invention includes a voice input receiving unit that receives input information with a voice, an output control unit that transmits the input information to a predetermined external device and then outputs a plurality of received content candidates according to order of a priority degree, and a content execution unit that executes, upon receipt of specification of any of the output content candidates, the content candidate.

According to the invention of the present application, a technology for starting appropriate content according to details input with a voice can be provided. Problems, configurations, and effects other than the above description will be revealed by description of the following embodiments.

BRIEF DESCRIPTION OF DRAWINGS

FIG. 4 is a diagram illustrating a data structure of a keyword storage unit;

FIG. 6 is a diagram illustrating a data structure of a priority category storage unit;

FIG. 8 is a diagram illustrating a data structure example during processing of a related word temporary storage unit;

FIG. 9 is a diagram illustrating a data structure example (No. 1) during processing of a content priority degree temporary storage unit;

FIG. 10 is a diagram illustrating a data structure example (No. 2) during processing of the content priority degree temporary storage unit;

FIG. 15 is a diagram illustrating a data structure of a word conversion table storage unit.

DETAILED DESCRIPTION

Hereinafter, an information system to which an embodiment according to the present invention is applied will be described with reference to the drawings. Note that FIGS. 1 to 13 do not illustrate all configurations of the information system, and a part of the configurations is appropriately omitted for easy understanding and description is given.

Figure 1:
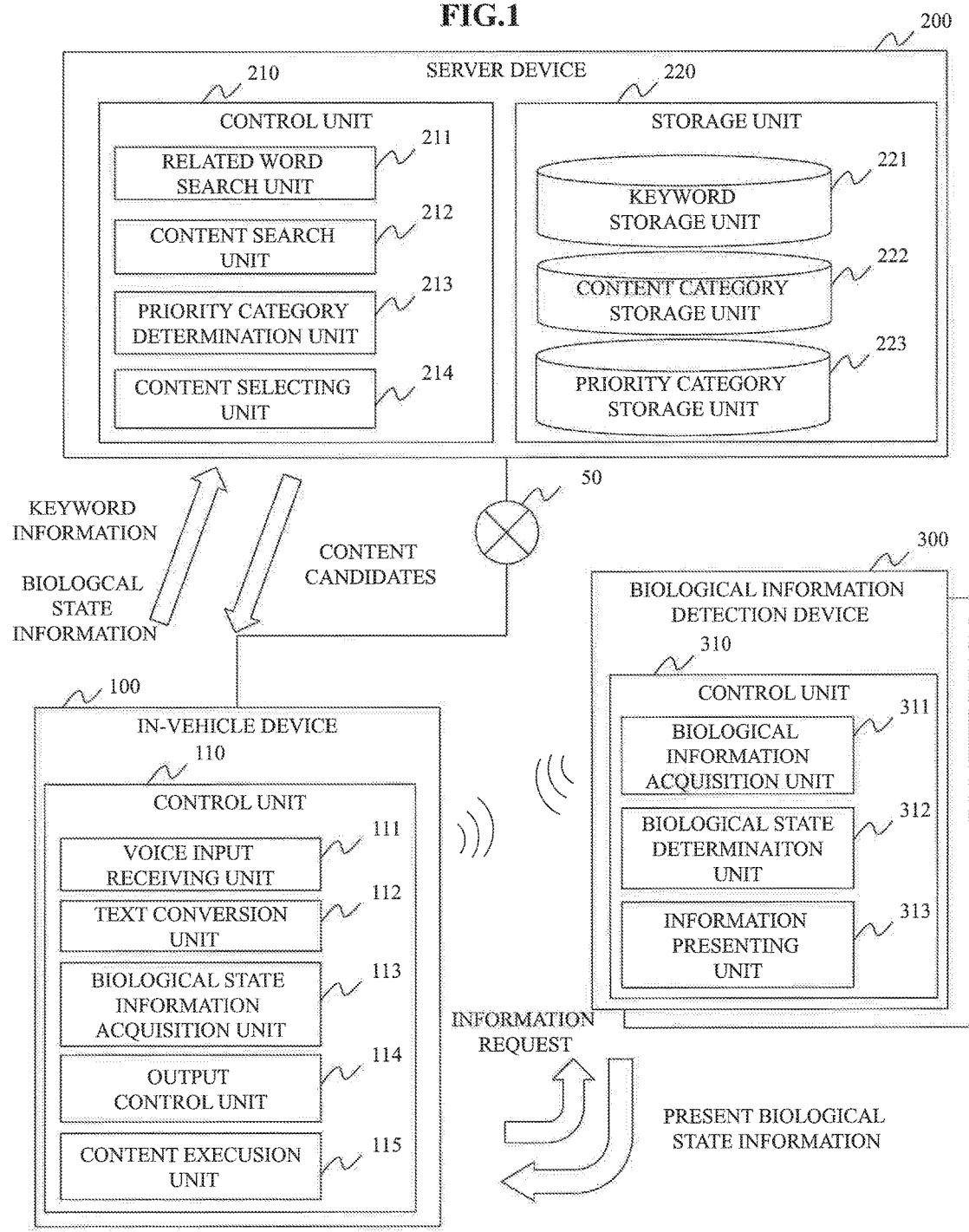
FIG. 1 is a diagram illustrating a structure of an information system according to a first embodiment.

FIG. 1 illustrates a structure of an information system according to a first embodiment. In the present information system, an in-vehicle device 100 and a server device 200 are communicatively connected through a network 50. The network 50 is desirably a public wireless communication network such as the Internet or a mobile phone network, for example. However, the network 50 may be a closed communication network provided in each predetermined managed area. To be specific, the network 50 is a communication network by any of various communication methods such as wireless networks including the Internet, a local area network (LAN), a wide area network (WAN), and a Wi-Fi (registered trademark), and short-distance wireless communication such as Bluetooth (registered trademark).

The in-vehicle device 100 is an information processing device mounted in a vehicle and can perform predetermined communication with another device mounted in the vehicle. In the present embodiment, the in-vehicle device 100 is a navigation system that can acquire current position information, route information, and the like. However, the in-vehicle device 100 as an object of the invention of the present application is not limited to the in-vehicle device 100 illustrated in FIG. 1. For example, the in-vehicle device 100 may be any of various control devices incorporated in a moving body. Further, the in-vehicle device 100 may be detachably provided in the vehicle. Alternatively, the in-vehicle device 100 may be a moving terminal such as a mobile telephone device held by a driver or an occupant of the vehicle, and may be a smart phone, a feature phone, a personal digital assistance (PDA), a notebook computer, a tablet terminal, or the like.

The in-vehicle device 100 is communicatively connected with one or a plurality of biological information detection devices 300 by wireless or wired means. The in-vehicle device 100 requests the biological information detection device 300 to present information, and receives biological state information as a response. Note that the biological state information in the present embodiment is a result about information that indicates states (for example, arousal level decrease, attention distraction, bad health, and the like) of a biological body determined by the biological information detection device 300 based on values of various sensors detected by the biological information detection device 300. However, the biological state information is not limited thereto, and may be the values of the various sensors themselves (for example, the number of blinks, a pulse, a body temperature, and the like) detected by the biological information detection device 300.

The in-vehicle device 100 is configured from a control unit 110. The control unit 110 includes a voice input receiving unit 111, a text conversion unit 112, a biological state information acquisition unit 113, an output control unit 114, and a content execution unit 115.

The voice input receiving unit 111 receives a voice input from a user. The text conversion unit 112 decomposes the voice input received by the voice input receiving unit 111 into words, performs voice recognition, and converts the words into texts on a word-by-word basis and the texts into a character string. Note that the text conversion unit 112 may transit voice information to another device through the network 50, for example, and have the another device perform the text conversion, and obtain the texts by receiving text information after the conversion.

The biological state information acquisition unit 113 performs communication with the biological information detection device 300 that detects biological information with a predetermined sensor to acquire biological state information of a biological body such as a user. Note that this communication may be any of various types of wireless communication such as Bluetooth (registered trademark) and near field communication (NFC).

The output control unit 114 transmits voice information (or voice information converted into texts) received by the voice input receiving unit 111 to the server device 200, and then outputs a plurality of content candidates received from the server device 200 in order of a priority degree of the content candidates. As an output screen, various screens can be expected. However, an output screen like a half-screen content candidate presenting screen 500 illustrated in FIG. 11 or a full-screen content candidate presenting screen 600 illustrated in FIG. 12 may be employed. Respective examples of the screens will be described below.

The content execution unit 115 executes the content candidate upon receipt of specification of any of the content candidates output by the output control unit 114. For example, in a case where the specified content is route search, the content execution unit 115 displays an initial input screen of processing for performing route search and starts the route search processing, and controls the route search processing. Further, the content to be executed is not limited to reproduction outputs of general music, still images, moving images, or documents, and includes dynamic outputs by various types of application software of service area/parking area (SA/PA) search, side road search, rest spot search, local gourmet search, and bathroom search.

Figure 2:
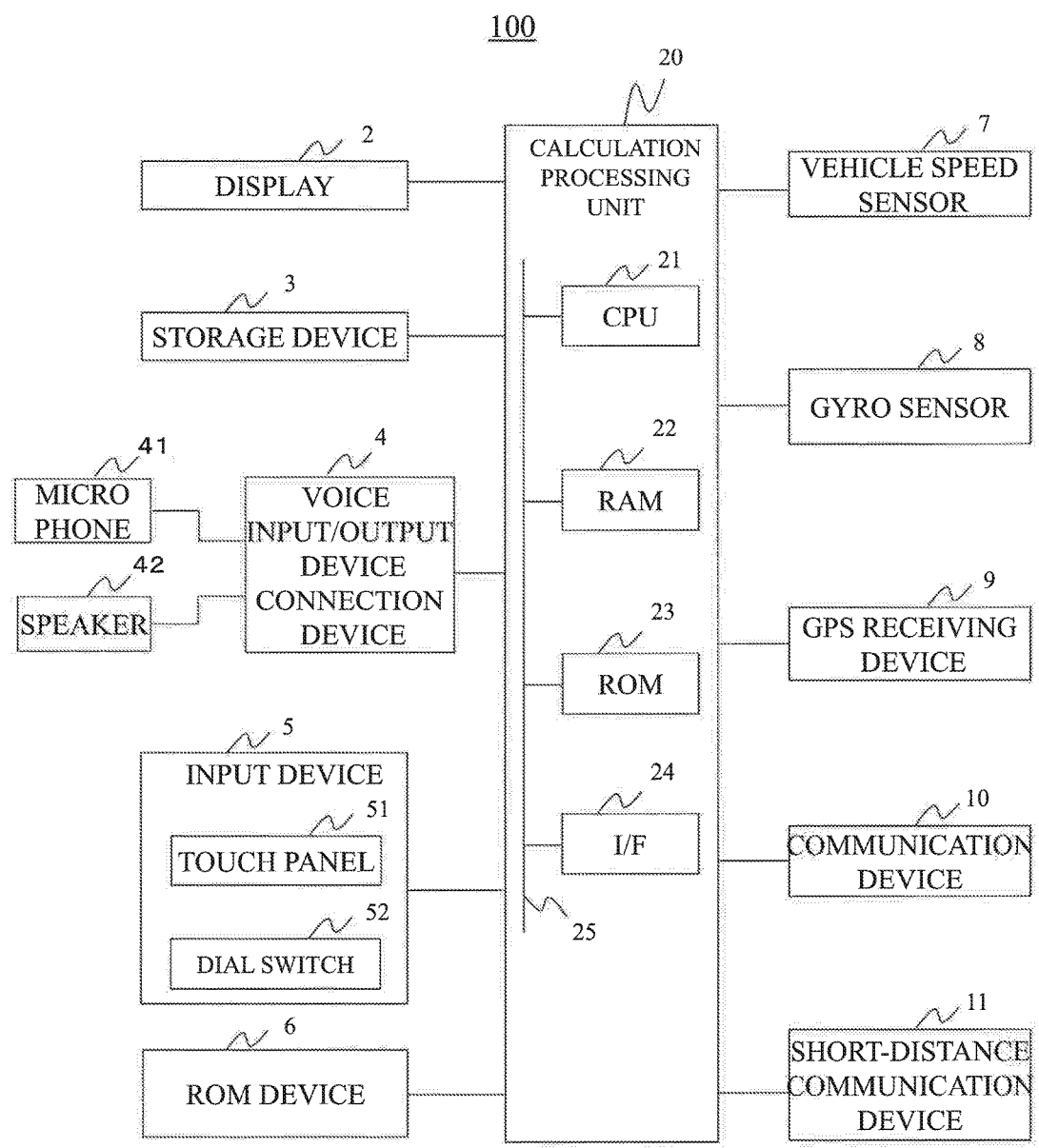
FIG. 2 is a diagram illustrating a structure of an in-vehicle device according to the first embodiment.

FIG. 2 is a diagram illustrating a structure of the in-vehicle device 100. The in-vehicle device 100 includes a calculation processing unit 20, a display 2, a storage device 3, a voice input/output device connection device 4 (including a microphone 41 as a voice input device and a speaker 42 as a voice output device), an input device 5 (including a touch panel 51 and a dial switch 52 as contact input devices), a read only memory (ROM) device 6, a vehicle speed sensor 7, a gyro sensor 8, a global positioning system (GPS) receiving device 9, a communication device 10, and a short-distance communication device 11.

The calculation processing unit 20 is a central unit that performs various types of processing. For example, the calculation processing unit 20 calculates a current place based on information output from the various sensors 7 and 8, the GPS receiving device 9, the communication device 10, the short-distance communication device 11, and the like. Further, the calculation processing unit 20 reads map data necessary for display from the storage device 3 or the ROM device 6 based on obtained information of the current place.

Further, the calculation processing unit 20 develops the read map data into graphics, superimposes a mark that indicates the current place on the map, and displays a superimposed image on the display 2. Further, the calculation processing unit 20 searches for a recommended route that is an optimum route connecting the current place or a departure point instructed by a user and a destination (or a transit point or a stop-over point) using the map data stored in the storage device 3 or the ROM device 6. Further, the calculation processing unit 20 guides the user using the speaker 42 and the display 2. Note that the calculation processing unit 20 performs types of processing described below, which are respectively executed by the functional units of the control unit 110 of the in-vehicle device 100, that is, the voice input receiving unit 111, the text conversion unit 112, the biological state information acquisition unit 113, the output control unit 114, and the content execution unit 115.

The calculation processing unit 20 of the in-vehicle device 100 has a configuration in which the devices are connected with a bus 25. The calculation processing unit 20 includes a central processing unit (CPU) 21 that executes various types of processing such as calculation of numerical values and control of the devices, a random access memory (RAM) 22 that stores the map data, the calculation data, and the like read from the storage device 3, a ROM 23 that stores programs and data, and an interface (I/F) 24 for connecting various types of hardware and the calculation processing unit 20.

The display 2 is a unit that displays graphic information generated in the calculation processing unit 20 and the like. The display 2 is configured from any of various display devices such as a liquid crystal display and an organic electro luminescence (EL) display.

The storage device 3 is configured from at least a readable/writable storage medium such as a hard disk drive (HDD), a solid state drive (SSD), or a non-volatile memory card.

In the storage medium, map information that is map data (including link data of a link that configures roads on the map) necessary for a regular route search device is stored.

The voice input/output device connection device 4 is connected with the microphone 41 as the voice input device and the speaker 42 as the voice output device, and converts the microphone 41 and the speaker 42 usable. The microphone 41 acquires a voice outside the in-vehicle device 100 such as a voice uttered by the user or another passenger.

The speaker 42 outputs a message generated in the calculation processing unit 20 to the user as a voice. The microphone 41 and the speaker 42 are separately arranged in predetermined portions of the vehicle. However, the microphone 41 and the speaker 42 may be housed in an integral housing. The in-vehicle device 100 can include a plurality of the microphones 41 and the speakers 42.

The input device 5 is a device that receives an instruction from the user through an operation with a hand of the user. The input device 5 is configured from the touch panel 51, the dial switch 52, a scroll key that is another hard switch (not illustrated), a scale change key, and the like. Further, the input device 5 includes a remote controller that can remotely operate and instruct the in-vehicle device 100. The remote controller includes a dial switch, a scroll key, a scale change key, and the like, and can send information of the operated keys and switches to the in-vehicle device 100.

The touch panel 51 is mounted on a display surface side of the display 2, and can allow a display screen to be seen through. The touch panel 51 identifies a touched position corresponding to XY coordinates of the image displayed on the display 2, converts the touched position into coordinates, and outputs the coordinates. The touch panel 51 is configured from a pressure-sensitive or electrostatic input detecting element, or the like. Note that the touch panel 51 may realize multi-touch that can detect a plurality of touched positions at the same time.

The dial switch 52 is configured to be rotatable in a clockwise direction or an anti-clockwise direction, generates a pulse signal for each predetermined angle of rotation, and outputs the pulse signal to the calculation processing unit 20. The calculation processing unit 20 obtains a rotation angle from the number of the pulse signals.

The ROM device 6 is configured from at least a readable storage medium such as a ROM including a CD-ROM or DVD-ROM, or an integrated circuit (IC) card. In this storage medium, for example, moving image data, voice data, and the like are stored.

The vehicle speed sensor 7, the gyro sensor 8, and the GPS receiving device 9 are used to detect the current place (for example, an own vehicle position) in the in-vehicle device 100. The vehicle speed sensor 7 is a sensor that outputs a value used to calculate a vehicle speed. The gyro sensor 8 is configured from an optical fiber gyro, a vibration gyro, or the like, and detects an angular speed by rotation of the moving body. The GPS receiving device 9 measures the current place, a traveling speed, and a traveling direction of the moving body by receiving signals from GPS satellites, and measuring distances between the moving body and the GPS satellites and change rates of the distances, about three or more satellites.

The communication device 10 starts, continues, and terminates communication with an access control device that is communicative with the server device 200. The communication device 10 is connected with the access control device by any of various communication methods such as the wireless network including the Internet, the LAN, the WAN, and the Wi-Fi (registered trademark), and the short-distance wireless communication such as Bluetooth (registered trademark). Further, the communication device 10 attempts discover of or connection with the access control device periodically or at predetermined timing, and establishes the communication with the connectable access control device.

The short-distance communication device 11 controls detection of a connection partner, establishment of connection, transfer control, connection discard, and the like about the short-distance wireless communication with another device such as the biological information detection device 300. For the short-distance wireless communication, any of various types of communication methods such as Bluetooth and NFC can be used. Note that the short-distance communication device 11 may be connected to an in-vehicle communication network such as a controller area network (CAN) by wired manner.

The above-described functional units of the control unit 110 of the in-vehicle device 100, that is, the voice input receiving unit 111, the text conversion unit 112, the biological state information acquisition unit 113, the output control unit 114, and the content execution unit 115 are built by read and execution of predetermined programs by the CPU 21. Therefore, the programs for realizing the processing of the functional units are stored in the RAM 22.

Note that the above-described configuration elements are configurations of the in-vehicle device 100 classified according to principal processing details, for easy understanding. Therefore, the invention of the present application is not limited by the way of classification of the configuration elements and names thereof. The configuration of the in-vehicle device 100 can be classified into a larger number of configuration elements according to the processing details. Further, one configuration element can be classified to execute a large number of types of processing.

Further, the functional units may be built by another hardware resource (an ASIC or a GPU), other than the CPU. Further, the processing of the functional units may be executed by a single hardware resource or a plurality of hardware resources.

The server device 200 is an information processing device configured from a control unit 210 and a storage unit 220. The server device 200 provides, upon receipt of a request to present content including keyword information, or the keyword information and the biological state information, from the in-vehicle device 100, information of the content candidate according to the request.

The storage unit 220 of the server device 200 includes a keyword storage unit 221, a content category storage unit 222, and a priority category storage unit 223.

The control unit 210 of the server device 200 includes a related word search unit 211, a content search unit 212, a priority category determination unit 213, and a content selecting unit 214.

FIG. 4 is a diagram illustrating a data structure of the keyword storage unit 221. In the keyword storage unit 221, a word, and a word and content related to the word are stored in association with each other.

In the keyword storage unit 221, a word number 221A, a word 221B, a related content name 221C, and a related word number 221D are stored in association with one another.

In the word number 221A, a number uniquely allocated in advance to the word stored in the word 221B is stored.

In the word 221B, information of a character string converted from the word is stored.

In the related content name 221C, information that identifies a name of the content related to the word stored in the word 221B is stored.

In the related word number 221D, information that identifies a word number that identifies another word associated with the word stored in the word 221B is stored. Note that, in the related word number 221D, numbers that identify one or a plurality of the related words can be stored.

Figure 5:
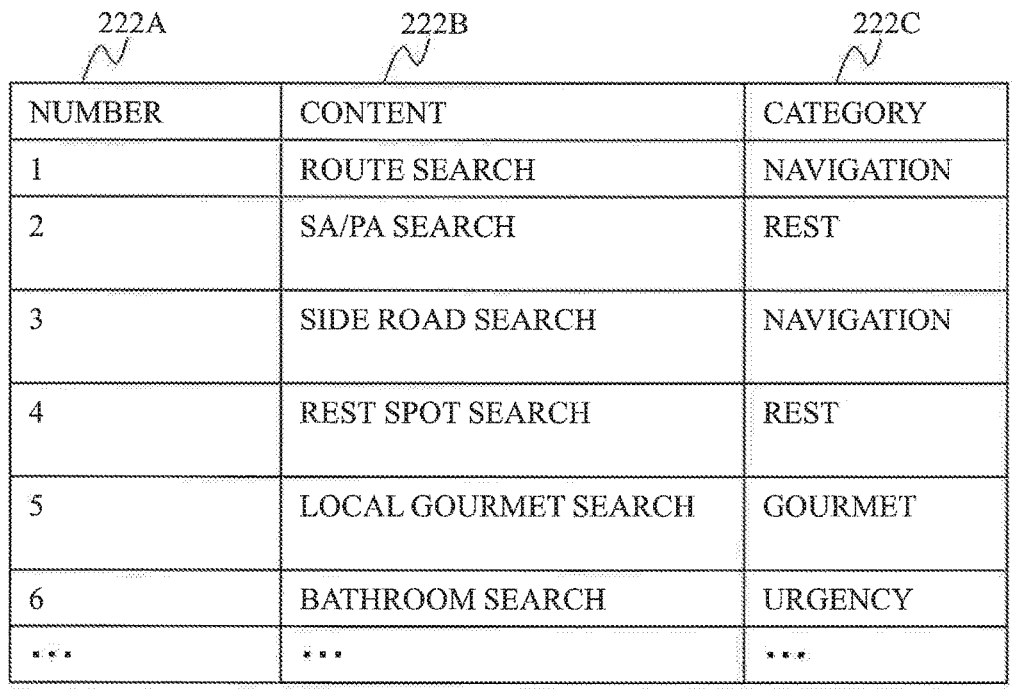
FIG. 5 is a diagram illustrating a data structure of a content category storage unit.

FIG. 5 is a diagram illustrating a data structure of the content category storage unit 222. In the content category storage unit 222, the content and its category are stored in association with each other.

In the content category storage unit 222, a number 222A, content 222B, and a category 222C are stored in association with one another.

In the number 222A, a number uniquely allocated in advance to the content stored in the content 222B is stored.

In the content 222B, content of an application or a presentation layer, such as programs of various functions and a uniform resource identifier (URI) of a web site, is stored. Note that the content may include the search content such as the route search, the service area/parking area (SA/PA) search, the side road search, the rest spot search, the local gourmet search, and the bathroom search, as described above.

In the category 222C, predetermined classification information according to a type of the content stored in the content 222B is stored. For example, the category includes navigation, rest, gourmet, urgency, and the like, and one piece of content belongs to one category. However, exceptionally, there may be content included in a plurality of categories.

FIG. 6 is a diagram illustrating a data structure of the priority category storage unit 223. In the priority category storage unit 223, the biological state information, a category to be prioritized, and information that identifies an increase amount of the priority degree are stored in association with one another.

In the priority category storage unit 223, a number 223A, biological state information 223B, a category to be prioritized 223C, and a priority degree increase amount 223D are stored in association with one another.

In the number 223A, a number uniquely allocated in advance to the biological state information stored in the biological state information 223B is stored.

In the biological state information 223B, information that indicates a state of the biological body is stored. Note that the biological state information may include information in which the types of states such as arousal level decrease, bad health, and attention distraction, as described above, and degree information that indicates the degree of the states (for example, in A to C three stages, where A is the most serious) are combined.

In the category to be prioritized 223C, a category of predetermined content according to the biological state information stored in the biological state information 223B is stored.

In the priority degree increase amount 223D, information that identifies the degree of increasing the priority degree is stored about the category of the predetermined content according to the biological state information stored in the biological state information 223B.

Referring back to description of FIG. 1. The related word search unit 211 included in the control unit 210 of the server device 200 recognizes, upon receipt of the information input with a voice, a word included in the information input with a voice as an input word, and identifies a directly related word related to the input word and an indirectly related word related to the directly related word using the keyword storage unit 221. That is, the related word search unit 211 collects a plurality of related keywords as candidates by searching for the word in two stages.

The content search unit 212 identifies content associated with the input word, and the directly related word and the indirectly related word identified by the related word search unit 211 using the keyword storage unit 221.

The priority category determination unit 213 identifies, upon receipt of the biological state information, the category associated in the priority category storage unit 223 and the increase amount of the priority degree of the category, and increases the priority degree of the content identified by the content search unit 212 according to the category of the content.

The content selecting unit 214 transmits one or a plurality of pieces of the content identified by the content search unit 212 to the in-vehicle device 100 together with the priority degree.

The biological information detection device 300 is an information processing device configured from a control unit 310. The biological information detection device 300 presents, upon receipt of an information request from the in-vehicle device 100, the biological state information according to the request.

The control unit 310 of the biological information detection device 300 includes a biological information acquisition unit 311, a biological state determination unit 312, and an information presenting unit 313.

The biological information acquisition unit 311 periodically or continuously acquires the biological information through a sensor for acquiring various types of biological information included in the biological information detection device 300.

The biological state determination unit 312 determines the state of the biological body according to a predetermined rule using the biological information acquired by the biological information acquisition unit 311. For example, the state of the biological body may include the information in which the types of states such as arousal level decrease, bad health, and attention distraction, as described above, and degree information that indicates the degree of the states (for example, in A to C three stages, where A is the most serious) are combined.

The information presenting unit 313 presents the biological state determined by the biological state determination unit 312 to the external device that has requested the information, for example, to the in-vehicle device 100.

Figure 3:
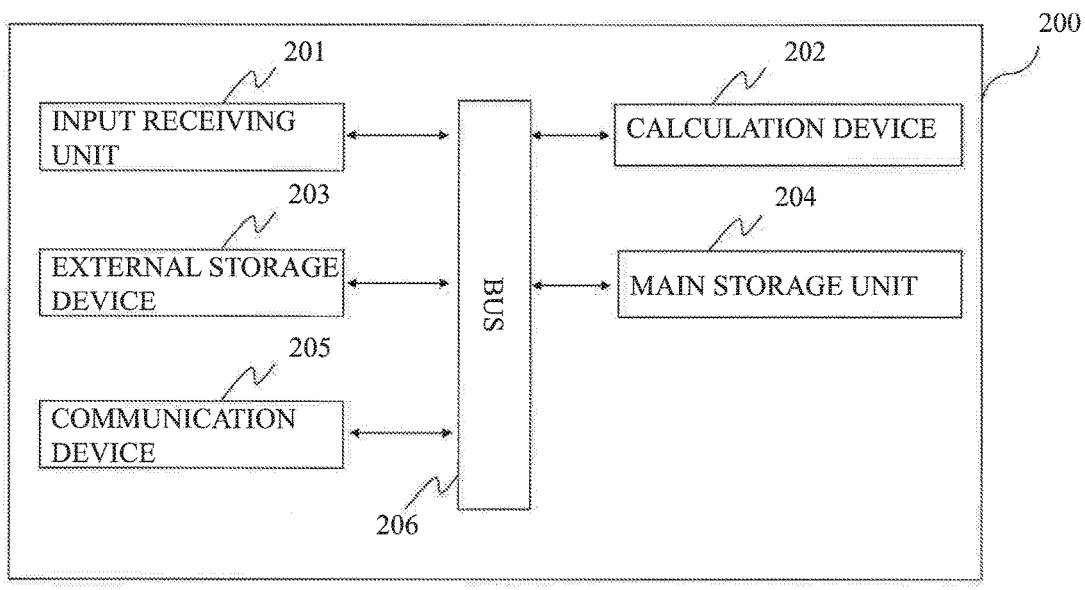
FIG. 3 is a diagram illustrating a hardware structure of a server device.

FIG. 3 is a diagram illustrating a hardware structure of the server device 200. The server device 200 is configured from an input receiving device 201, a calculation device 202, an external storage device 203, a main storage device 204, a communication device 205, and a bus 206 that connects the aforementioned devices.

The above-described functional units of the control unit 210, that is, the related word search unit 211, the content search unit 212, the priority category determination unit 213, and the content selecting unit 214 are built by read and execution of predetermined programs by the calculation device 202. Therefore, the programs for realizing the processing of the functional units are stored in the main storage device 204 or the external storage device 203.

Note that the above-described configuration elements are configurations of the server device 200 classified according to principal processing details, for easy understanding. Therefore, the invention of the present application is not limited by the way of classification of the configuration elements and its names. The configuration of the server device 200 can be classified into a larger number of configuration elements according to the processing details. Further, one configuration element can be classified to execute a larger number of types of processing.

Further, the functional units may be built by a hardware resource (an ASIC or a GPU), other than the CPU. Further, the processing of the functional units may be executed by a single hardware resource or may be executed by a plurality of hardware resources.

[Description of Operation]

Next, an operation of content execution processing performed by the in-vehicle device 100 and the server device 200 will be described.

Figure 7:
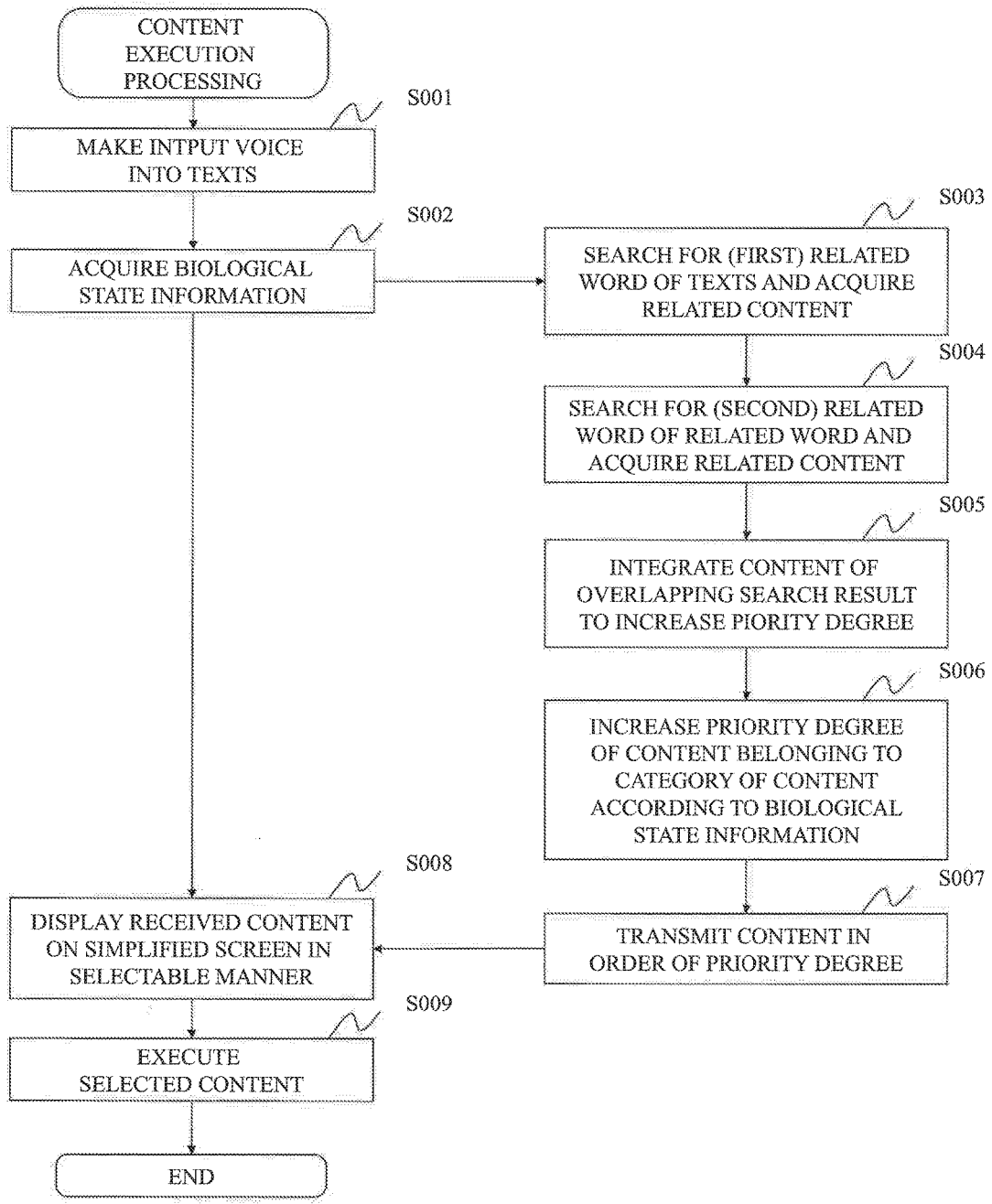
FIG. 7 is a diagram illustrating a flow of content execution processing.

FIG. 7 is a diagram illustrating a flow of the content execution processing. The content execution processing is started in response to a voice input from the user or at predetermined timing.

First, the voice input receiving unit 111 and the text conversion unit 112 convert the input voice into texts (step S001). To be specific, the text conversion unit 112 decomposes the voice received by the voice input receiving unit 111 of the in-vehicle device 100 into words and recognizes the words, converts the recognized word into texts, and recognizes the texts as the keyword information. At that time, as described above, the text conversion unit 112 may transmit the voice information to another device, and receive the texts that are a result returned from the another device.

The biological state information acquisition unit 113 then acquires the biological state information from the biological information detection device 300 (step S002). To be specific, the biological state information acquisition unit 113 requests the biological information detection device 300 to present the biological information, and the information presenting unit 313 of the biological information detection device 300 presents the information that indicates the biological state determined by the biological state determination unit 312. Note that, in a case where a plurality of the biological information detection devices 300 is communicatively connected with the in-vehicle device 100, all of the communicative biological information detection devices 300 present the biological state information, and the biological state information acquisition unit 113 acquires all of the biological state information. However, an embodiment is not limited thereto, and the biological state information acquisition unit 113 may acquire the information only from the biological information detection device 300 that satisfies a predetermined condition.

The output control unit 114 then transmits the information that is the voice information received by the voice input receiving unit 111 and converted into texts (that is, the keyword information) and the biological state information acquired by the biological state information acquisition unit 113 to the server device 200.

The related word search unit 211 of the server device 200 searches for a (first) related word of the texts, and acquires the related content (step S003). To be specific, the related word search unit 211 recognizes each word of the transmitted texts as the input word, and identifies the directly related word related to the input word using the keyword storage unit 221. Note that, as for the specification of the directly related word, the related word search unit 211 searches for the word 221B of the keyword storage unit 221 using the input word as a key, reads the related word number 221D and the related content name 221C associated with the appropriate word, and then reads the word of the number identified in the related word number 221D from the word 221B, thereby to identify the word as the directly related word.

The related word search unit 211 then searches for a (second) related word of the related word, and acquires the related content (step S004). To be specific, the related word search unit 211 identifies, for each identified directly related word, the indirectly related word related to the directly related word using the keyword storage unit 221. Note that, as for the specification of the indirectly related word, the related word search unit 211 searches for the word 221B of the keyword storage unit 221 using the directly related word as a key, reads the related word number 221D and the related content name 221C associated with the appropriate word, and then reads the word of the number identified in the related word number 221D from the word 221B, thereby to identify the word as the indirectly related word.

FIG. 8 is a diagram illustrating a data structure example during processing of the related word temporary storage unit 225. The related word temporary storage unit 225 is temporarily configured in a predetermined variable area or the like on the main storage device 204. The related word temporary storage unit 225 is configured from an input word 225A, a first related word 225B, a second related word 225C, a related content name 225D, and a category 225E in association with one another.

For example, the word input with a voice and transmitted from the in-vehicle device 100 is stored in the input word 225A. The directly related word is stored in the first related word 225B. The indirectly related word is stored in the second related word 225C. Further, names of the related content for respective words in the input word 225A, the first related word 225B, and the second related word 225C are stored in the related content name 225D. The name of the category to which the related content name 225D belongs is stored in the category 225E.

Next, the priority category determination unit 213 integrates the content having overlapping search results to increase the priority degree (step S005). To be specific, the priority category determination unit 213 reads the content stored in the related content name 225D in step S004 and its category 225E to the content priority degree temporary storage unit 226 illustrated in FIG. 9, and increases the priority degree according to the number of pieces of the overlapping content.

FIG. 9 is a diagram illustrating a data structure example (No. 1) during processing of the content priority degree temporary storage unit 226. In the content priority degree temporary storage unit 226, content 226A, a category 226B, and a priority degree 226C are stored in association with one another. Here, the content stored in the related content name 225D in step S004 and its category 225E are respectively stored to the content 226A and the category 226B. Further, in the priority degree 226C, a value that indicates the priority degree is stored for each content (the content with a higher priority degree is prioritized over the content with a lower priority degree).

When the priority category determination unit 213 then detects the content overlapping with the information stored in the content 226A, the priority category determination unit 213 increases the priority degree according to the number of pieces of the overlapping content, and narrows down the overlapping content to one to eliminate the overlapping. Note that the increased priority degree 226C may be simply calculated as a total value of the priority degrees, or may be a sequentially recorded increase amount.

Referring back to the description of FIG. 7, the priority category determination unit 213 increases the priority degree of the content belonging to the category of the content according to the biological state information (step S006). To be specific, the priority category determination unit 213 searches for the biological state information 223B of the priority category storage unit 223 using the biological state information transmitted in step S002 as a key, and reads the prioritized category 223C and the priority degree increase amount 223D of the appropriate information. The priority category determination unit 213 then searches for the category 226B of the content priority degree temporary storage unit 226 using the read prioritized category as a key, and increases the priority degrees 226C of all pieces of the appropriate content according to the increase amount. Note that, when the priority category determination unit 213 acquires a plurality of pieces of the biological state information, that is, when one biological information detection device 300 presents the biological state information that indicates a plurality of the biological states, or when a plurality of the biological information detection devices 300 presents the biological state information that indicates each of the plurality of biological states, the priority category determination unit 213 increases the priority degrees about a predetermined number of pieces of the biological state information in ascending order of the number 223A of the priority category storage unit 223.

FIG. 10 is a diagram illustrating a data structure example (No. 2) during processing of the content priority degree temporary storage unit 226. That is, FIG. 10 is a specific example of processing for increasing the priority degree of the category according to the biological state. When the biological state information corresponds to an increase of the priority degree of a rest category by 3, the priority category determination unit 213 increases the priority degree 226E and the priority degree 226F of the content (the SA/PA search and the rest spot search in FIG. 10) that belong the category of rest by 3.

The content selecting unit 214 then transmits the content in order of the priority degree (step S007). To be specific, the content selecting unit 214 sorts the content in descending order of the priority degree 226C of the content priority degree temporary storage unit 226, acquires the content 226A and its priority degrees 226C corresponding to a predetermined number of pieces (for example, four pieces) from the top, and transmits the content 226A and its priority degrees 226C to the in-vehicle device 100. Note that the content selecting unit 214 may transmit the content 226A and the priority degrees 226C of all of the pieces.

The output control unit 114 of the in-vehicle device 100 then selectively displays the received content on a simplified screen (step S008). To be specific, the output control unit 114 configures a content presenting screen illustrated in FIG. 11 or 12, and outputs the content presenting screen to the display 2.

Figure 11:
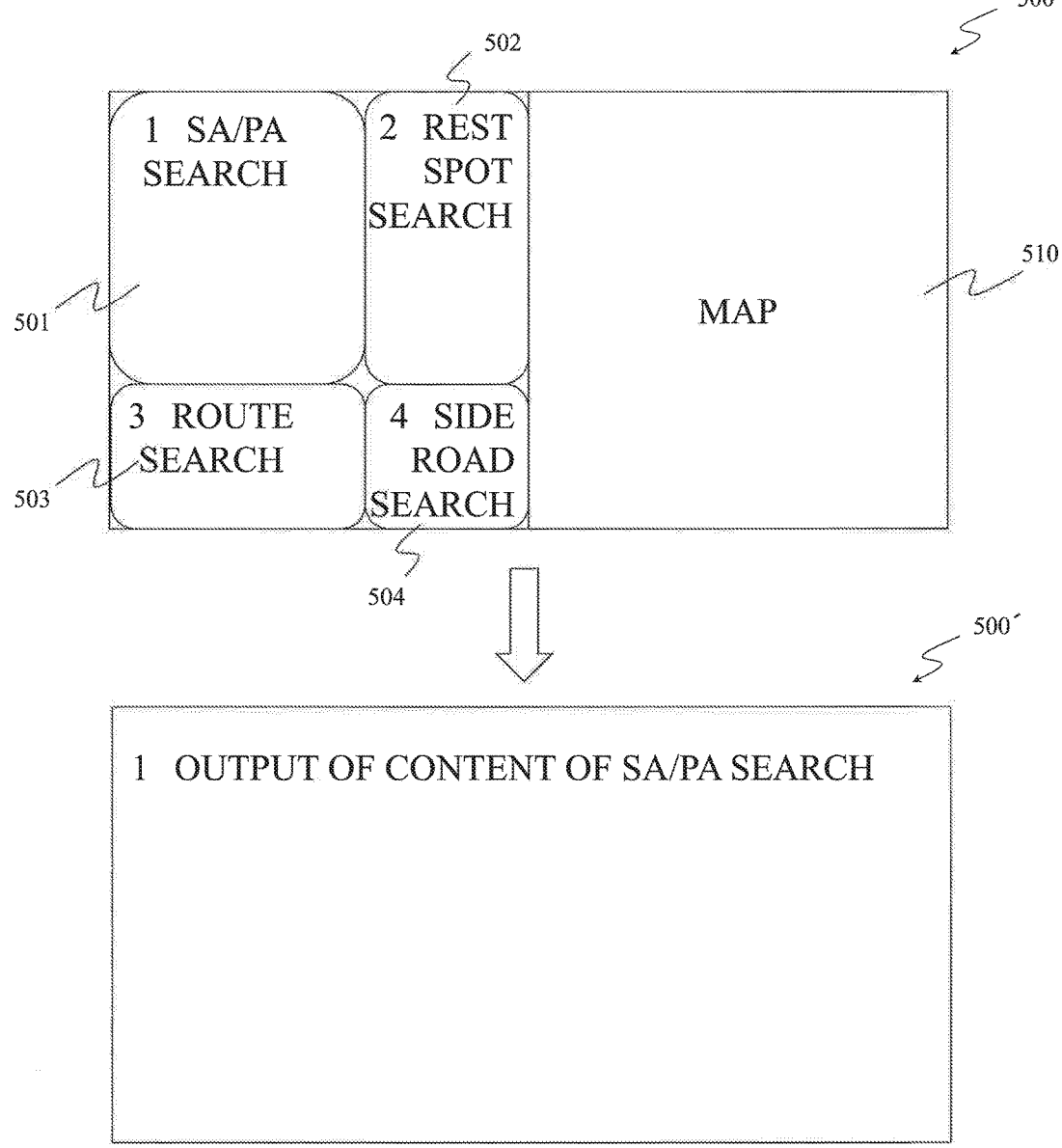
FIG. 11 is a diagram illustrating an example of a half-screen content candidate presenting screen.

FIG. 11 is a diagram illustrating an example of a half-screen content candidate presenting screen 500. On the half-screen content candidate presenting screen 500, the content (SA/PA search 501, rest spot search 502, route search 503, and side road search 504) is displayed on a predetermined simplified screen such that the content with a higher priority degree occupies a larger display area on the left half of the screen, and an output by the function output prior to the voice input of the in-vehicle device 100 such as the map 510 is performed on the right half of the screen.

The content execution unit 115 then executes the selected content (step S009).

For example, the content execution unit 115 displays a content output screen 500' on which the content is executed with full-screen display when there is an input to select any of the content on the simplified screen on the half-screen content candidate presenting screen 500 of FIG. 11.

Figure 12:
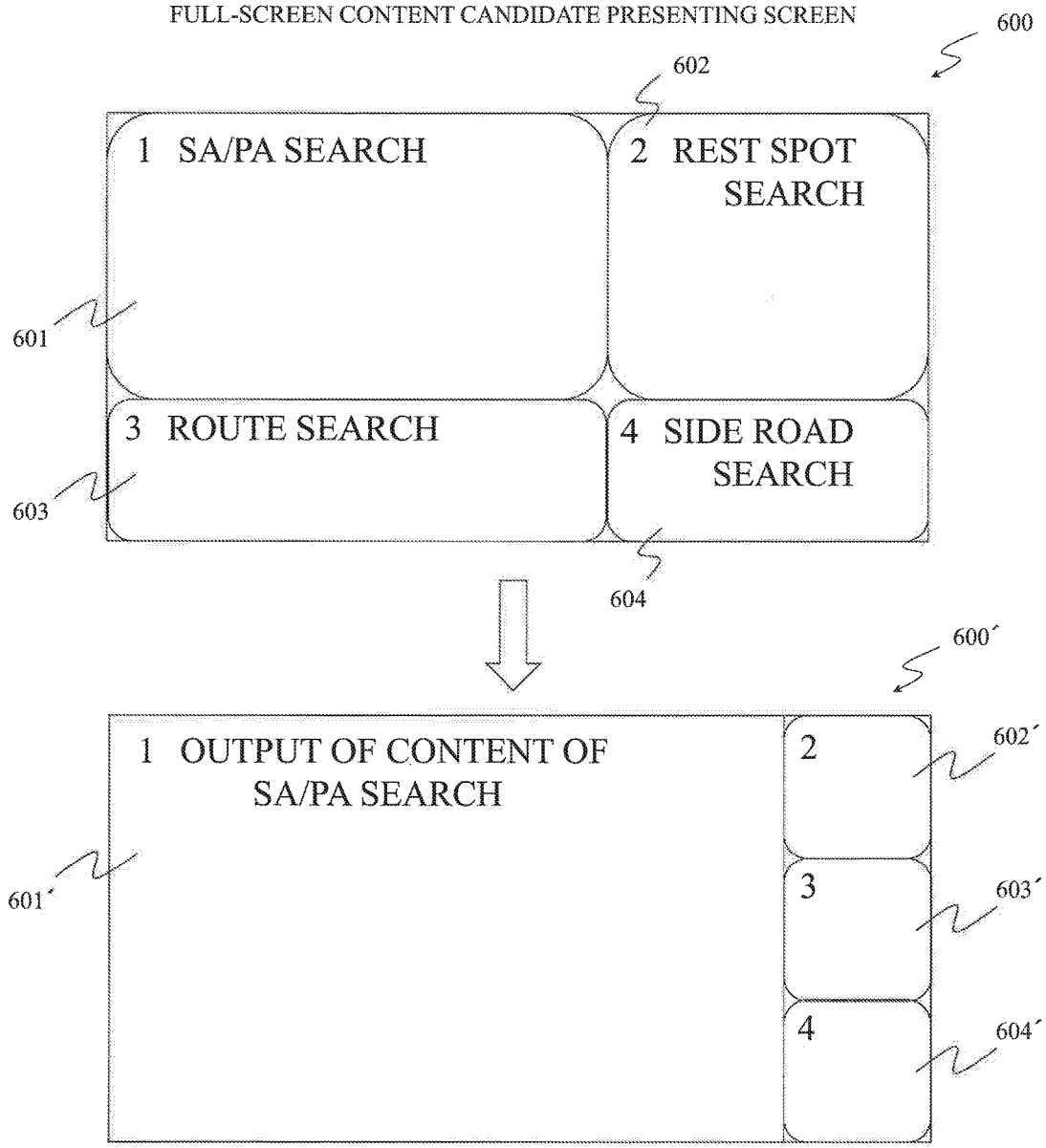
FIG. 12 is a diagram illustrating an example of a full-screen content candidate presenting screen.

FIG. 12 is a diagram illustrating an example of a full-screen content candidate presenting screen 600. On the full-screen content candidate presenting screen 600, the content (SA/PA search 601, rest spot search 602, route search 603, and side road search 604) are displayed on a predetermined simplified screen such that the content with a higher priority degree occupies a larger display area on the screen.

Then, for example, the content execution unit 115 displays a content output screen 600' on which the content is executed with a predetermined range of screen display when there is an input to select any of the content on the simplified screen on the full-screen content candidate presenting screen 600 of FIG. 12. Further, in this case, on the content output screen 600', a simplified screen of other pieces of content (rest spot search 602', route search 603', and side road search 604') is reduced to a predetermined region on the right end on the screen and displayed in a selectable manner.

The above is the flow of the content execution processing. According to the content execution processing, appropriate content can be started according to input details with a voice.

Figure 13:
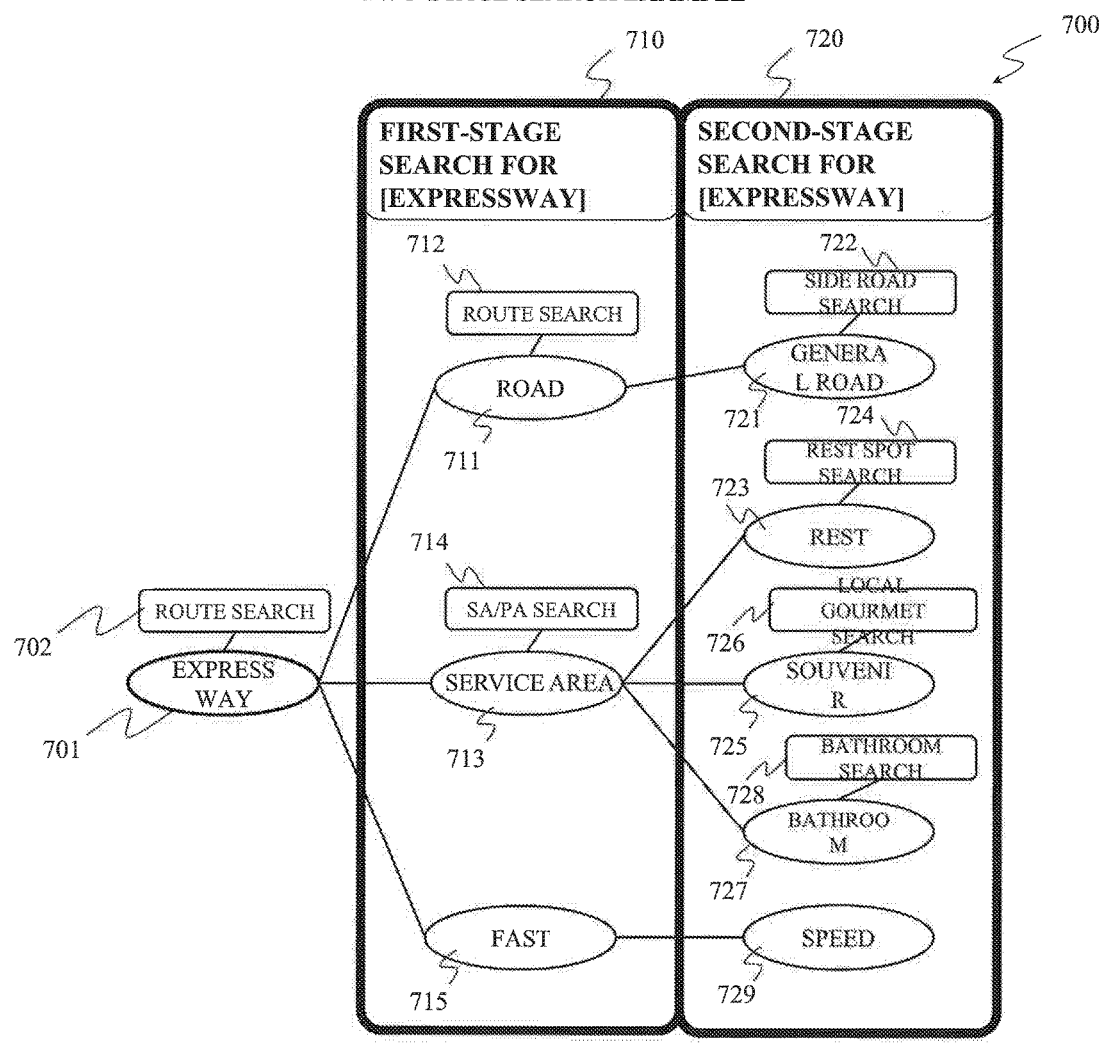
FIG. 13 is a diagram illustrating an example of two-stage search results.

FIG. 13 is a diagram illustrating an example of two-stage search results. In the content execution processing, two-stage word search including the directly related word that is directly related to the input word and the indirectly related word related to the directly related word is performed, and the related content is recognized as object content to be executed. The schematic diagram 700 illustrates a specific example of such search. That is, relationship among "expressway" that is an input word 701 and corresponding "route search" content 702, first-stage search 710, and second-stage search 720 is illustrated. The first-stage search 710 includes "road" 711 that is a directly related word directly related to the input word 701 and corresponding "route search" content 712, a directly related word "service area" 713 and corresponding "SA/PA search" content 714, and a directly related word "fast" 715. The second-stage search 720 includes "general road" 721 that is an indirectly related word related to the directly related word and corresponding "side road search" content 722, an indirectly related word "rest" 723 and corresponding "rest spot search" content 724, an indirectly related word "souvenir" 725 and corresponding "local gourmet search" content 726, an indirectly related word "bathroom" 727 and corresponding "bathroom search" content 728, and an indirectly related word "speed" 729.

By searching for the related content in two stages in this way, the range of the candidates of the content, execution of which is potentially desired by the user can be appropriately expanded. In addition, in consideration of the biological state information, execution of the function potentially desired by the user can be appropriately supported.

The above is the information system according to the first embodiment. According to the first embodiment, appropriate content can be started according to the details input with a voice.

Note that the present invention is not limited to the above embodiment. Various modifications can be made in the first embodiment within the technical idea of the present invention.

For example, in the first embodiment, the in-vehicle device 100 receives the input of a voice, acquires the biological state information, and presents the content candidates. However, the embodiment is not limited thereto. For example, an application may be operated on a smart phone communicatively connected to the in-vehicle device 100, and execute the above processing.

For example, in the first embodiment, the control unit 110 included in the in-vehicle device 100 may be realized by a control unit of a smart phone connected to the in-vehicle device 100.

Further, the in-vehicle device 100 passes the input information to the smart phone upon receipt of an input to the smart phone, and performs an output upon receipt of an output instruction from the smart phone. That is, the in-vehicle device 100 plays a role of a user interface of the smart phone.

Further, in such a modification, for example, by enabling specification of a device of an output destination in the output control unit of the smart phone, outputs can be respectively instructed to the in-vehicle device 100 and the smart phone with different output details. To be specific, output information (for example, static content) by simple application software, which only presents acquired information, is output to the smart phone, and output information (for example, dynamic content) by complicated application software, which receives an input from a user and performs processing such as input processing of search, and outputs a result of the processing, is output to the in-vehicle device 100. In doing so, a result of the simple acquisition of information may be accumulated in the smart phone, and details may be confirmed at arbitrary timing after the user gets off the vehicle. In doing so, non-urgent information can be confirmed by the driver in a relaxed way after driving.

Further, by outputting the output information related to privacy information only to the smart phone when there is a plurality of passengers, the privacy information of a person who wears the biological information detection device can be prevented from being notified to other passengers. As for this method, an existing known method can be employed, such as a method for identifying the number of persons using a seating sensor or an in-vehicle camera for grasping the number of passengers, or a method for identifying the number of persons by wireless communication connection with a device close to an owner of the smart phone. The output control unit outputs the output information either to the smart phone or the in-vehicle device 100 depending on whether the number of passengers to the vehicle is a predetermined number.

Further, for example, in the above-described embodiment, the content to be executed by the server device 200 is narrowed down in the in-vehicle device 100 using the voice input as a trigger. However, an embodiment is not limited thereto. For example, the narrowing down may be performed with a gesture (action). In this case, the in-vehicle device 100 receives a load input of each axial direction by an acceleration sensor for detecting the gesture, and performing text conversion in advance according to meaning of the gesture, thereby to realize the narrowing down.

Further, for example, the content to be executed may be narrowed down according to the biological state information, gesture information, vehicle information flowing in CAN, or information related to a surrounding environment obtained through a camera or the Internet.

Figure 14:
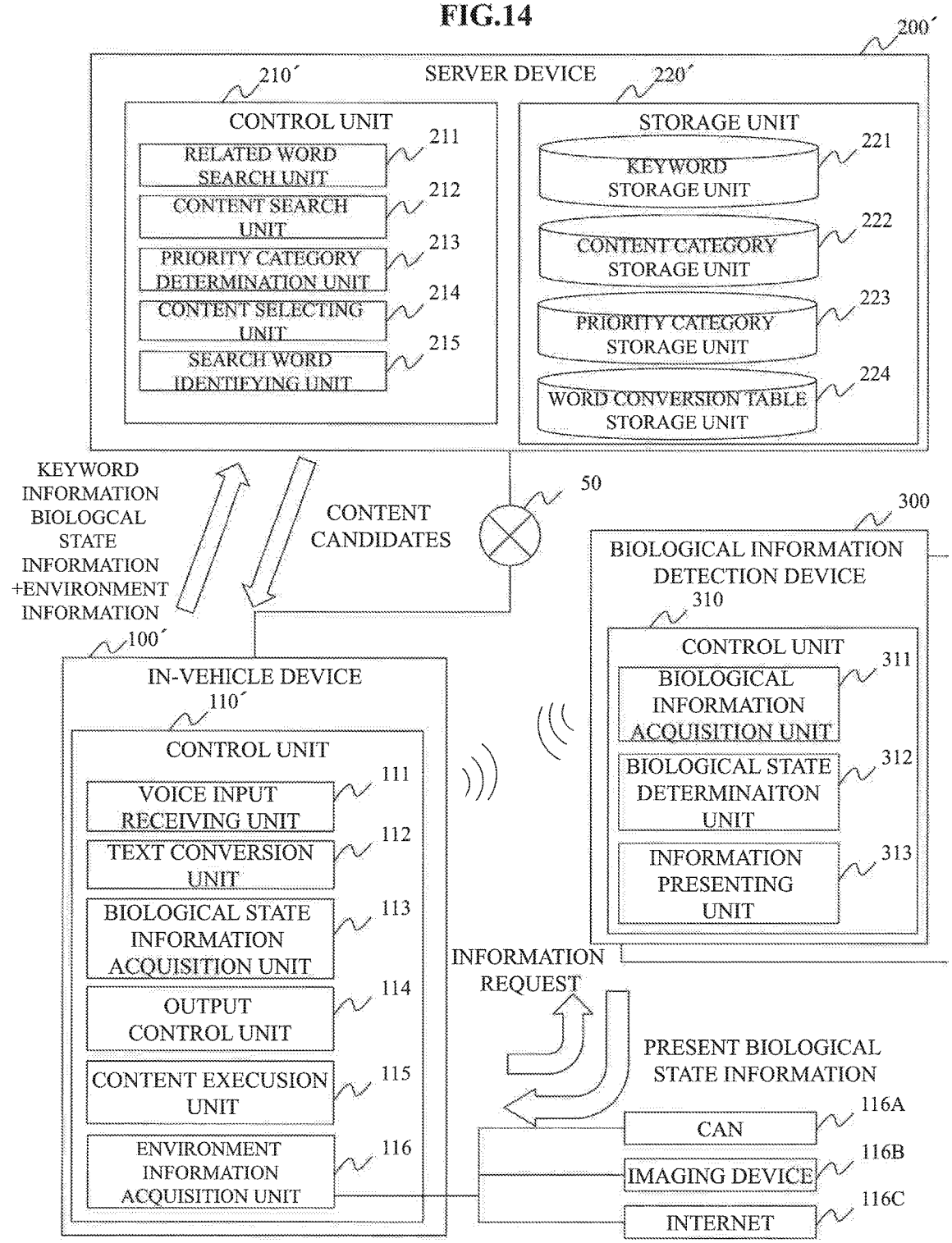
FIG. 14 is a diagram illustrating a structure of an information system according to a second embodiment.

FIG. 14 is a diagram illustrating a structure of an information system according to a second embodiment related to the aforementioned modifications. The second embodiment has an approximately similar configuration to the first embodiment. However, a part of the configuration is different. Hereinafter, the different points will be mainly described.

In the information system according to the second embodiment, an in-vehicle device 100' including an environment information acquisition unit 116 in a control unit 110' is used in place of the in-vehicle device 100. The environment information acquisition unit 116 acquires predetermined environment information from a CAN 116A that is an information source related to an environment existing outside the in-vehicle device 100', an imaging device 116B, and other devices on the Internet 116C.

For example, the environment information acquisition unit 116 acquires information such as a vehicle speed, an ON/OFF state of windshield wiper, an ON/OFF state of headlights, a driving time, a time to destination, traffic jam information, a gas remaining amount from the CAN 116A at predetermined timing, for example, in every fixed period. Further, for example, the environment information acquisition unit 116 acquires information such as existence/non-existence of an object that may become an obstacle in front from the imaging device 116B at predetermined timing, for example, in every fixed period. Further, for example, the environment information acquisition unit 116 acquires information such as a temperature and disaster warnings from the Internet 116C at predetermined timing, for example, in every fixed period. Alternatively, in a case where a driver uploads the biological state information onto a predetermined server on the Internet 116C, the environment information acquisition unit 116 may acquire the biological state information. Further, for example, the environment information acquisition unit 116 acquires information of acceleration of each axis from the above-described acceleration sensor that detects a gesture at predetermined timing, for example, in every fixed period. Further, the environment information acquisition unit 116 transmits the acquired environment information to a server device 200'.

Further, in the information system according to the second embodiment, the server device 200' in which a search word identifying unit 215 is included in a control unit 210' and a word conversion table storage unit 224 is included in a storage unit 220' is used in place of the server device 200. In the word conversion table storage unit 224, the environment information, its threshold, a word employed when exceeding the threshold are stored in association with one another in advance. By use them, the search word identifying unit 215 receives the environment information and determines the threshold, acquires a word as text information, about the environment information that exceeds the threshold, as a result of the determination, and recognizes the text information as keyword information.

FIG. 15 is a diagram illustrating a data structure of the word conversion table storage unit 224. In the word conversion table storage unit 224, a number 224A, environment information 224B, a threshold 224C that serves as a reference to detect change in the environment information 224B, and a word 224D employed as the keyword information when the change is detected are stored in association with one another.

In the number 224A, a number uniquely allocated in advance to a combination of the environment information 224B and the threshold 224C is stored.

In the environment information 224B, the environment information including the biological state information, the gesture information, the vehicle information flowing in the CAN, and the information related to surrounding environment obtained through a camera or the Internet are stored.

In the threshold 224C, threshold information that serves as a reference of detection of change in the information stored in the environment information 224B is stored. For example, as for the environment information 224B of "vehicle speed", change of an average value from less than 70 (kilometer per hour) to 70 (kilometer per hour) or more is the threshold information that serves as the reference of detection.

In the word 224D, the text information applied as a keyword when the environment information stored in the environment information 224B is changed beyond the threshold stored in the threshold 224C is stored. For example, as for the example of the vehicle speed, the text information of "expressway" is associated as the keyword information.

Figure 16:
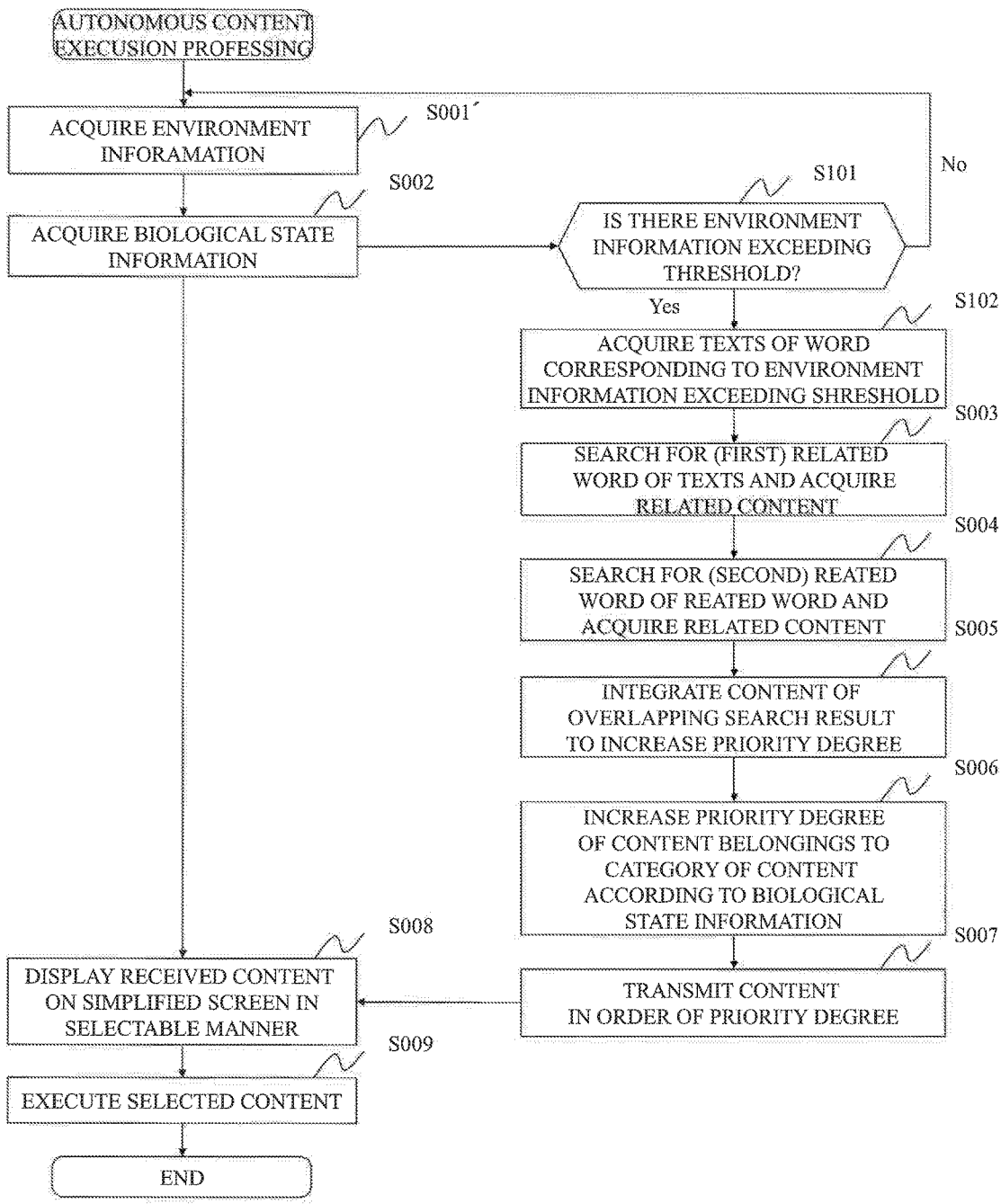
FIG. 16 is a diagram illustrating a flow of autonomous content execution processing.

FIG. 16 is a diagram illustrating a flow of autonomous content execution processing. The autonomous content execution processing is periodically started when the in-vehicle device 100' is started.

The autonomous content execution processing according to the second embodiment is basically approximately similar to the content execution processing of the first and second embodiments. However, a part of the processing is different. Hereinafter, the different points will be mainly described.

First, the environment information acquisition unit 116 acquires the environment information (step S001'). To be specific, the environment information acquisition unit 116 sends an information acquisition request to any or all of the CAN 116A, the imaging device 116B, and the Internet 116C, and acquires replied environment information.

Note that, in step S002, an output control unit 114 transmits the environment information and the biological state information acquired by a biological state information acquisition unit 113 to the server device 200'.

Then, the search word identifying unit 215 of the server device 200' determines whether there is the environment information exceeding the threshold (step S101). To be specific, the search word identifying unit 215 determines whether there is the transmitted environment information that is matched with the environment information 224B of the word conversion table storage unit 224, and satisfies the threshold 224C. When there is none ("No"), the search word identifying unit 215 returns the control to step S001'.

When there is the environment information exceeding the threshold ("Yes" in step S101), the search word identifying unit 215 acquires texts of a word corresponding to the environment information exceeding the threshold (step S102). To be specific, the search word identifying unit 215 reads the word 224D of the word conversion table storage unit 224 about the environment information exceeding the threshold, and recognizes the word as the keyword information.

Hereinafter, processing similar to the content execution processing in the first and second embodiments is performed.

The above processing is the autonomous content execution processing according to the second embodiment. According to the autonomous content execution processing, the in-vehicle device can suggest execution of the content according to change of the environment information without waiting for an explicit voice input instruction by the user. Accordingly, the usability can be enhanced taking a demand of the user in advance.

As described above, the present invention has been described using the first and second embodiments. However, the embodiments are not limited thereto, and the characteristic processing described in the embodiments can be applied to other devices (for example, the characteristic processing can be applied not only to the in-vehicle device 100, but also to mobile terminals such as attachable/detachable navigation devices).

What is claimed is:

1. An in-vehicle device comprising:
    a voice input/output connection device including a microphone that receives a voice from a user and a speaker that outputs a voice message to the user;
    an input device including at least one of a touch panel and a dial switch that receives an instruction from the user;
    a central processing unit programmed to
        receive input information from the voice input/output connection device including the voice from the user;
        convert the received input information into text information and identify keywords corresponding to the text information;
        transmit the input information to a predetermined external device, including a keyword storage unit configured to store a word in association with a word and content related to the word; a control unit programmed to recognize, upon receipt of information input with a voice, a word included in the information input with a voice as an input word, and identify a directly related word related to the input word and an indirectly related word related to the directly related word, but not included in the information input with the voice, using the keyword storage unit, identify pieces of content respectively associated with the input word, the directly related word and the indirectly related word, using the keyword storage unit, and transmit one or a plurality of the pieces of the content to the in-vehicle device for display to a user; a priority category storage unit configured to store biological state information indicating a state of a biological body in association with a category obtained by classifying the content candidates; and a priority category determination unit configured to identify the category associated by the priority category storage unit upon receipt of the biological state information, and set a priority order to the content candidates identified according to the category of the content candidates, receive from the external device the plurality of content candidates according to the priority order of the content candidates that is based on the category of the biological state information indicating the state of the biological body, and then output the plurality of content candidates according to the priority order of the content candidates; and
        execute, upon receipt of specification from the input device of any of the output content candidates, the content candidate; and
    a display that displays the plurality of content candidates according to the priority order of the content candidates.

2. The in-vehicle device according to claim 1, wherein the central processing unit displays a display area of the content candidate larger as the order of the priority degree is higher.

3. The in-vehicle device according to claim 1, wherein the central processing unit acquires the biological state information indicating the state of the biological body from an external biological information detection device, and
    the central processing unit transmits the biological state information to the external device.

4. The in-vehicle device according to claim 1, wherein the central processing unit programmed to:
    acquire environment information, and
    transmit the environment information to the external device.

5. The in-vehicle device according to claim 1, wherein the biological state information includes at least one of arousal level decrease, attention distraction, and bad health of the biological body.

6. A server device comprising:
    a keyword storage unit configured to store a word in association with a word and content related to the word;
    a control unit programmed to
        recognize, upon receipt of information input with a voice, a word included in the information input with a voice as an input word, and identify a directly related word related to the input word and an indirectly related word related to the directly related word, but not included in the information input with a voice, using the keyword storage unit;
        identify pieces of content respectively associated with the input word, the directly related word and the indirectly related word, using the keyword storage unit; and transmit one or a plurality of the pieces of the content to an external device, including a voice input/output connection device including a microphone that receives the voice from a user and a speaker that outputs a voice message to the user, an input device including at least one of a touch panel and a dial switch that receives an instruction from the user, a central processing unit programmed to receive input information from the voice input/output connection device including the voice from the user, convert the received input information into text information and identify keywords corresponding to the text information, transmit the input information to the server device, receive from the server device a plurality of content candidates according to a priority order of the content candidates that is based on a category of biological state information, and then output the plurality of content candidates according to the priority order of the content candidates, and execute, upon receipt of specification from the input device of any of the output content candidates, the content candidate, and a display that displays the plurality of content candidates according to the priority order of the content candidates, for display to the user;

a priority category storage unit configured to store the biological state information indicating a state of a biological body in association with the category of the biological state information, which is obtained by classifying the content candidates; and a priority category determination unit configured to identify the category associated by the priority category storage unit upon receipt of the biological state information, and set the priority order to the content candidates identified according to the category of the content candidates.

7. The server device according to claim 6, further comprising:

a word conversion table storage unit configured to store environmental information identifying an environment in association with a keyword; wherein the control unit is programmed to identify, upon receipt of the environment information, the keyword associated with the environment information using the word conversion table storage unit, and recognize the keyword as the input word, and the control unit is programmed to identify the directly related word and the indirectly related word using the input word.

8. The server device according to claim 6, wherein the biological state information includes at least one of arousal level decrease, attention distraction, and bad health of the biological body.

9. An information system comprising:

an in-vehicle device; and a server device communicatively connected with the in-vehicle device, the in-vehicle device including a voice input/output connection device including a microphone that receives a voice from a user and a speaker that outputs a voice message to the user;

an input device including at least one of a touch panel and a dial switch that receives an instruction from the user;

a central processing unit programmed to receive input information from the voice input/output connection device including the voice from the user, convert the received input information into text information and identify keywords corresponding to the text information;

transmit the input information to the server device, receive from the server device a plurality of content candidates according to an order of a priority degree of the content candidates that is based on a category of biological body information, and then output the plurality of content candidates according to the order of the priority degree, and execute, upon receipt of specification from the input device of any of the output content candidates, the content candidate, and a display that displays the plurality of content candidates according to the order of the priority degree;

the server device including a keyword storage unit configured to store a word in association with a word and content related to the word;

a control unit programmed to recognize, upon receipt of information input with a voice, a word included in the input information as an input word, and identify a directly related word associated with the input word and an indirectly related word associated with the directly related word, but not included in the information input with a voice, using the keyword storage unit, identify pieces of content associated with the input word, and the directly related word and the indirectly related word using the keyword storage unit, and transmit one or a plurality of the pieces of content to the in-vehicle device as the content candidates;

a priority category storage unit configured to store biological state information indicating a state of a biological body in association with a category obtained by classifying the content candidates; and a priority category determination unit configured to identify the category associated by the priority category storage unit upon receipt of the biological state information, and set a priority order to the content candidates identified according to the category of the content candidates.

10. The information system according to claim 9, wherein the biological state information includes at least one of arousal level decrease, attention distraction, and bad health of the biological body.

11. A content start method of an in-vehicle device, the method comprising the steps of:

receiving input information with a voice from a voice input/output connection device, including a microphone that receives the voice from a user and a speaker that outputs a voice message to the user;

converting the received input information into text information and identifying keywords corresponding to the text information;

transmitting the input information to a predetermined external device, receiving from the external device a plurality of content candidates according to an order of a priority degree of the content candidates, and then outputting the plurality of content candidates according to the order of the priority degree;

executing, upon receipt of specification from an input device, including at least one of a touch panel and a dial switch that receives an instruction from the user, of any of the output content candidates, the content candidate;

displaying the plurality of content candidates according to the order of the priority degree;

recognizing, upon receipt of the input information with the voice, a word included in the input information as an input word, and identifying a directly related word associated with the input word and an indirectly related word associated with the directly related word, but not included in the input information with the voice, using a keyword storage unit identifying pieces of content associated with the input word, and the directly related word and the indirectly related word using the keyword storage unit;

transmitting one or a plurality of the pieces of content to the in-vehicle device as the content candidates;

storing biological state information indicating a state of a biological body in association with a category obtained by classifying the content; and identifying the category upon receipt of the biological state information, and setting priority order to the content identified according to the category of the content.

12. The method according to claim 11, wherein the biological state information includes at least one of arousal level decrease, attention distraction, and bad health of the biological body.

* * * * *